United States Patent
Sugimoto (10) Patent No.: US 8,310,664 B2
(45) Date of Patent: Nov. 13, 2012

(54) REFRACTIVE INDEX DISTRIBUTION MEASURING METHOD AND REFRACTIVE INDEX DISTRIBUTION MEASURING APPARATUS

(75) Inventor: Tomohiro Sugimoto, Minamisaitama-gun (JP)

(73) Assignee: Canon Kabushiki Kaisha (JP)

( * ) Notice: Subject to any disclaimer, the term of this patent is extended or adjusted under 35 U.S.C. 154(b) by 176 days.

(21) Appl. No.: 12/949,024

(22) Filed: Nov. 18, 2010

(65) Prior Publication Data
US 2011/0116081 A1 May 19, 2011

(30) Foreign Application Priority Data
Nov. 18, 2009 (JP) ................................. 2009-262468

(51) Int. Cl.
*G01N 21/41* (2006.01)
*G02B 3/00* (2006.01)
(52) U.S. Cl. ........ 356/128; 356/124; 356/630; 356/517; 359/654
(58) Field of Classification Search .......... 356/128–137, 356/517, 630; 359/196, 205, 654, 896
See application file for complete search history.

(56) References Cited

U.S. PATENT DOCUMENTS

| 4,565,449 A | * | 1/1986 | Grego ........................... 356/484 |
| 4,744,654 A | | 5/1988 | Jinno et al. |
| 5,151,752 A | | 9/1992 | Oono et al. |
| 5,526,118 A | * | 6/1996 | Miyagawa et al. ........... 356/484 |
| 5,557,408 A | * | 9/1996 | Kanaya ........................ 356/514 |
| 5,966,161 A | * | 10/1999 | Kato ............................. 347/258 |
| 7,345,826 B2 | * | 3/2008 | Suhara ......................... 359/654 |
| 2006/0262417 A1 | * | 11/2006 | Suhara ......................... 359/654 |

FOREIGN PATENT DOCUMENTS

| JP | 61-070436 A | 4/1986 |
| JP | 1-316627 A | 12/1989 |
| JP | 2-008726 A | 1/1990 |
| JP | 11-044641 A | 2/1999 |

* cited by examiner

*Primary Examiner* — Sang Nguyen
(74) *Attorney, Agent, or Firm* — Rossi, Kimms & McDowell LLP (57) ABSTRACT

The method includes first and second steps of placing an object in first and second media whose refractive indices are lower than that of the object, and of causing the reference light to enter the object to measure first and second transmitted wavefronts. When light rays entering a peripheral portion of the object and passing through a same point of the object are defined as first and second light rays, the method causes these light rays to proceed in directions mutually different to change an NA of the reference light such that the reference light after being transmitted through the object is brought closer to collimated light than that before entering the object. The method calculates an effective thickness of the object using geometric thicknesses thereof and calculates a refractive index distribution thereof using the first and second transmitted wavefronts and the effective thickness.

4 Claims, 4 Drawing Sheets

REFRACTIVE INDEX DISTRIBUTION MEASURING METHOD AND REFRACTIVE INDEX DISTRIBUTION MEASURING APPARATUS

BACKGROUND OF THE INVENTION

1. Field of the Invention

The present invention relates to a method and an apparatus for measuring a refractive index distribution of an object such as an optical element.

2. Description of the Related Art

Optical elements such as lenses that are used for optical apparatuses such as digital cameras and laser beam printers require high refractive indices. On the other hand, molding technology enables easy production of complex shapes such as aspheric surfaces even when using optical glasses and plastics having high refractive indices.

However, molding sometimes causes, inside the optical element, refractive index nonuniformity depending on molding conditions. Such internal refractive index nonuniformity greatly affects optical characteristics of the optical element, which may make it impossible to obtain desired optical characteristics. Therefore, highly accurate measurement of internal optical homogeneity of the optical element having a high refractive index is required.

Methods of measuring the optical homogeneity generally include interferometries that measure a transmitted wavefront of an object (optical element) highly accurately processed to measure an internal refractive index distribution thereof. Moreover, a method is proposed which places an object between glass plates and soaks the object in oil being provided therebetween and having a refractive index approximately equal to that of the object to reduce surface accuracy errors of the object.

Japanese Patent Laid-Open No. 01-316627 discloses a method which measures a transmitted wavefront of an object soaked in a medium (matching oil) having a refractive index approximately equal to that of the object to obtain optical properties of the object. This method enables measurement of an internal refractive index distribution of the object without accurate processing of the object.

Japanese Patent Laid-Open No. 02-008726 discloses a method which measures a transmitted wavefront of an object soaked in a first matching oil having a refractive index approximately equal to that of the object, and further measures a transmitted wavefront of the object soaked in a second matching oil having a refractive index slightly different from that of the object. The disclosed method obtains a shape and a refractive index distribution of the object based on the transmitted wavefronts measured with the first and second matching oils.

In the measurement with the second matching oil, influences of the refractive index distribution and shape of the object appear as interference fringes on a detector for measuring the transmitted wavefront. Therefore, it is necessary that the refractive index of the second matching oil be slightly different from that of the object within a range where the interference fringes are not exceedingly thickened.

The measuring methods disclosed in Japanese Patent Laid-Open Nos. 01-316627 and 02-008726 need the matching oil having the refractive index approximately equal to that of the object. However, matching oils having high refractive indices generally have low transmittances. Therefore, when measuring a transmitted wavefront of an object whose refractive index is high by the measuring methods disclosed in Japanese Patent Laid-Open Nos. 01-316627 and 02-008726, the detector outputs only a small signal, which deteriorates measurement accuracy.

On the other hand, when using a low refractive index matching oil, aberrations caused due to the shape of the object are added to the transmitted wavefront. Moreover, since light being used for the measurement becomes non-collimated light, arrangement errors of optical elements other than the object also affect the transmitted wavefront. These make it difficult to accurately extract only the refractive index distribution from the transmitted wavefront.

SUMMARY OF THE INVENTION

The present invention provides a method and an apparatus capable of highly accurately measuring an internal refractive index distribution of a high refractive index object even when soaking the object in a low refractive index medium.

The present invention provides as one aspect thereof a refractive index distribution measuring method including a first measuring step of placing an object in a first medium whose refractive index is lower than a refractive index of the object, and of causing reference light to enter the object to measure a first transmitted wavefront of the object, a second measuring step of placing the object in a second medium whose refractive index is lower than the refractive index of the object and different from the refractive index of the first medium, and of causing the reference light to enter the object to measure a second transmitted wavefront of the object, and a calculating step of calculating an internal refractive index distribution of the object. When, of the reference light entering the object in the first measuring step, a light ray entering a peripheral portion of the object which is away from a central portion thereof which is located on an optical axis and passing through a certain point of the object is defined as a first light ray, and of the reference light entering the object in the second measuring step, a light ray entering the peripheral portion and passing through the certain point is defined as a second light ray, in the first and second steps the method causes the first and second light rays to proceed in directions different from each other to change a numerical aperture of the reference light such that the reference light after being transmitted through the object is brought closer to collimated light than the reference light before entering the object. Further, in the calculating step, the method calculates an effective thickness of the object by using geometric thicknesses of the object along the respective first and second light rays, and calculates the internal refractive index distribution of the object by using the first and second transmitted wavefronts measured in the first and second measuring steps and the calculated effective thickness.

The present invention provides as another aspect thereof a manufacturing method of an optical element including a forming step of molding the optical element, and an evaluating step of evaluating the optical element. In the evaluating step, the method measures the internal refractive index distribution of the optical element by using the above-described refractive index distribution measuring method.

The present invention provides as still another aspect thereof a refractive index distribution measuring apparatus including a measuring part configured to perform a first measurement that causes reference light to enter an object placed in a first medium whose refractive index is lower than a refractive index of the object to measure a first transmitted wavefront of the object, and to perform a second measurement that causes the reference light to enter the object placed in a second medium whose refractive index is lower than the refractive index of the object and different from the refractive index of the first medium to measure a second transmitted wavefront of the object, and a calculating part configured to calculate an internal refractive index distribution of the object. When, of the reference light entering the object in the first measurement, a light ray entering a peripheral portion of the object which is away from a central portion thereof which is located on an optical axis and passing through a certain point of the object is defined as a first light ray, and of the reference light entering the object in the second measurement, a light ray entering the peripheral portion and passing through the certain point is defined as a second light ray, the measuring part is configured to cause the first and second light rays to proceed in directions different from each other to change a numerical aperture of the reference light such that the reference light after being transmitted through the object is brought closer to collimated light than the reference light before entering the object. Further, the calculating part is configured to calculate an effective thickness of the object by using geometric thicknesses of the object along the respective first and second light rays, and calculates the internal refractive index distribution of the object by using the first and second transmitted wavefronts measured in the first and second measurements and the calculated effective thickness.

Other aspects of the present invention will become apparent from the following description and the attached drawings.

DETAILED DESCRIPTION OF THE EMBODIMENTS

Exemplary embodiments of the present invention will hereinafter be described with reference to the accompanying drawings.

Description will be first made of a refractive index distribution measuring apparatus which practices a refractive index distribution measuring method that is a first embodiment (Embodiment 1) of the present invention. The refractive index distribution measuring method of this embodiment measures transmitted wavefronts of the object soaked in two media (air and water in this embodiment as examples) whose refractive indices are lower than that of the object and different from each other to calculate an internal refractive index distribution of the object. In this embodiment, the object is an optical element such as a lens having a negative power as an example.

Figure 1A:
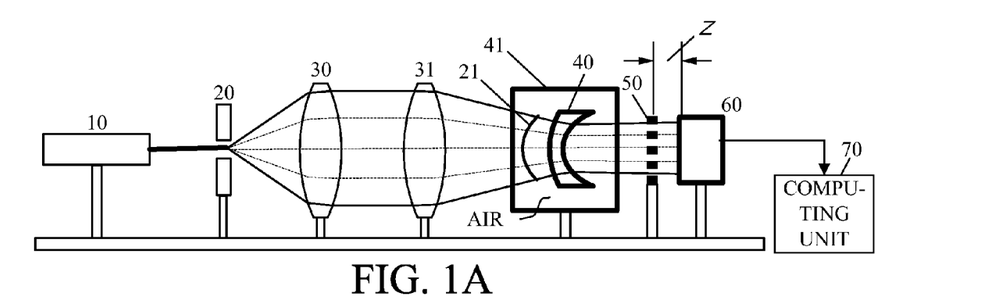
FIGS. 1A and 1B show a configuration of a refractive index distribution measuring apparatus practicing a refractive index distribution measuring method that is Embodiment 1 of the present invention.
Figure 1B:
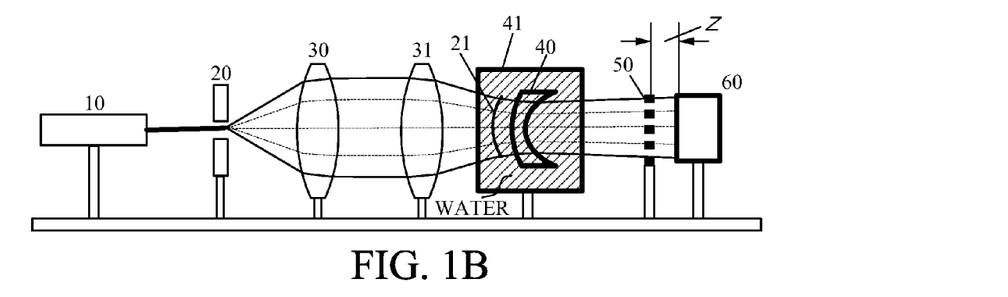

FIGS. 1A and 1B show a configuration of a Talbot interferometer (measuring part) that soaks an object 40 in air (first medium) and water (second medium) to measure transmitted wavefronts of the object 40. The object 40 is soaked in the air and the water inside an object case 41. The refractive indices of the air and the water are both lower than that of the object 40. Moreover, the refractive index of the water is higher than that of the air.

Laser light emitted from a laser light source (for example, a He—Ne laser) passes through a pinhole 20 to be diffracted thereat. A diameter φ of the pinhole 20 is designed to be small such that diffracted light can be regarded as an ideal spherical wave and further such that a numerical aperture (hereinafter referred to as "NA") of a first collimator lens 30 and a wavelength λ of the laser light source 10 satisfy the following expression:

$$\phi \approx \frac{\lambda}{NA} \qquad (1)$$

The diameter φ of the pinhole 20 can be set to about 2 μm in a case where the wavelength λ is 600 nm and the NA is about 0.3.

The laser light that has passed through the pinhole 20 is transmitted through the first collimator lens 30 and a second collimator lens 31 to be converged thereby. An optical system generating light that illuminates the object 40 is referred to as an "illumination optical system". In this embodiment, the pinhole 20, the first collimator lens 30 and the second collimator lens 31 constitute the illumination optical system.

The converged laser light passes through the air or the water in the object case 41 and then enters the object 40 to be transmitted therethrough. The laser light passing through the medium in the object case 41 and then entering the object 40 is referred to as "reference light". The reference light 21 is, of the light from the illumination optical system, only a light component that is actually transmitted through the object 40. In other words, the reference light 21 is not light components that are not transmitted through the object 40, such as a light component being reflected by the object case 41 and the object 40 due to their shapes.

The laser light (transmitted light) that has been transmitted through the air or the water in the object case 41 is brought to approximately collimated light, and passes through an orthogonal diffraction grating 50 that is a two-dimensional diffraction grating. Then, the transmitted light is captured (measured) by an image-pickup element 60, such as a CCD sensor or a CMOS sensor, which is a detector. The image-pickup element 60 is hereinafter referred to as the "CCD 60". When the NA of the transmitted light that has been transmitted through the object 40 is small, a distance Z between the diffraction grating 50 and the CCD 60 satisfying the following Talbot condition (2) generates on the CCD 60 interference fringes as a self-image of the diffraction grating 50:

$$\frac{Z_0 Z}{Z_0 - Z} = \frac{md^2}{\lambda} \quad (2)$$

In the expression (2), Z represents the distance between the diffraction grating 50 and the CCD 60, which is hereinafter referred to as "Talbot distance". Moreover, m represents a natural number, and d represents a grating pitch of the diffraction grating 50. $Z_0$ represents a distance from the diffraction grating 50 to an image plane of the object 40. A sign of the distance $Z_0$ is positive in a direction from the diffraction grating 50 toward the CCD 60. When the transmitted light that has been transmitted through the object 40 is approximately collimated light, the Talbot distance Z corresponds to a value at $Z_0=\infty$ in the expression (2). The grating pitch d of the diffraction grating 50 is set depending on an amount of aberration of the object 40.

Figure 2:
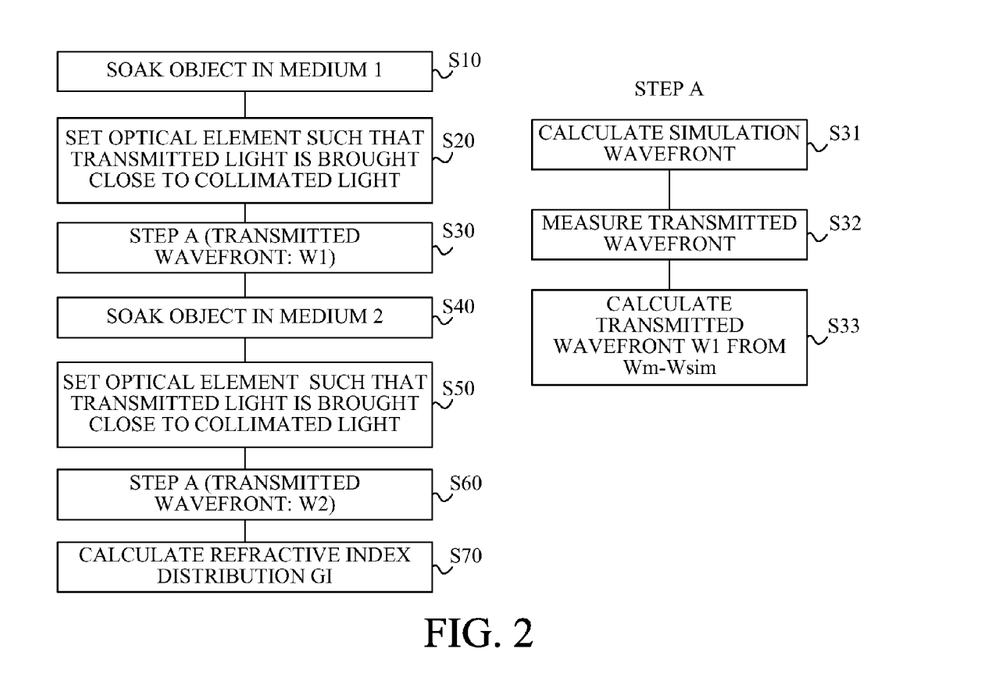
FIG. 2 is a flowchart showing a refractive index distribution calculating procedure in Embodiment 1.

FIG. 2 shows a procedure for calculating an internal refractive index distribution GI of the object 40 using an image captured by the CCD 60. In the procedure, calculation processing is executed according to a computer program by a computing unit (calculating part) 70 shown in FIG. 1A such as a microcomputer.

First, as shown in FIG. 1A, the procedure fills an inside of the object case 41 with the air, and places the object 40 therein (step S10). The air is shown as "MEDIUM 1" in FIG. 2.

Next, the procedure changes the NA of the reference light 21 such that the reference light (transmitted light) after being transmitted through the object 40 is brought closer to collimated light than the reference light before entering the object 40 (step S20). The NA of the reference light 21 can be changed by adjusting a position of the second collimator lens 31 (that is, a distance between the second collimator lens 31 and the object 40) in an optical axis direction while monitoring a light intensity distribution of the transmitted light through the CCD 60. The second collimator lens 31 corresponds to an optical element closest to the object 40 among optical elements constituting the illumination optical system.

The NA of the reference light 21 does not mean an NA of the reference light immediately after being transmitted through the illumination optical system, but means an NA of the reference light in the medium. The monitoring of the light intensity distribution of the transmitted light may be performed by using a scattering element such as a screen, instead of the CCD 60. Instead of the monitoring of the light intensity distribution of the transmitted light, the second collimator lens 31 and the object 40 may be arranged based on a value designed such that the transmitted light is brought close to collimated light.

Then, the procedure (calculation processing) calculates, according to step A which will be described later, a first transmitted wavefront (first wavefront aberration) $W_1$ when the medium in the object case 41 is the air (step S30). Step A includes the following three steps.

In step A, the calculation processing first calculates a simulation wavefront $W_{sim}$ when the object 40 soaked in the air is assumed to have an ideal internal refractive index distribution (step S31). This step S31 is a step of independently calculating a transmitted wavefront in a state where arrangement of the second collimator lens 31 and the object 40 is the same as that in step 20 and an even refractive index distribution is provided to the inside of the object 40. Such an object whose refractive index is even is referred to as a "reference object". In other words, the simulation wavefront $W_{sim}$ is a transmitted wavefront corresponding to the reference object.

Figure 3A:
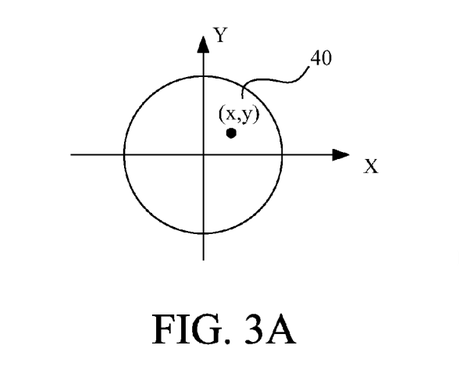
FIGS. 3A and 3B show a coordinate system defined on an object and an optical path in the refractive index distribution measuring apparatus in Embodiment 1.

The simulation wavefront $W_{sim}$ at a point (x, y) in the object 40 shown in FIG. 3A is expressed by the following expression (3). The expression (3) ignores a thickness of a wall of the object case 41 for simplification. The wall of the object case 41 is formed of a light-transmissive material such as glass.

$$W_{sim} = \{L_{1a}(x,y) + N_1 L_{1b}(x,y) + N(0,0)L_1(x,y) + N_1 L_{1c}(x,y) + L_{1d}(x,y)\} - \{L_{1a}(0,0) + N_1 L_{1b}(0,0) + N(0,0)L_1(0,0) + N_1 L_{1c}(0,0) + L_{1d}(0,0)\} \quad (3)$$

Figure 3B:
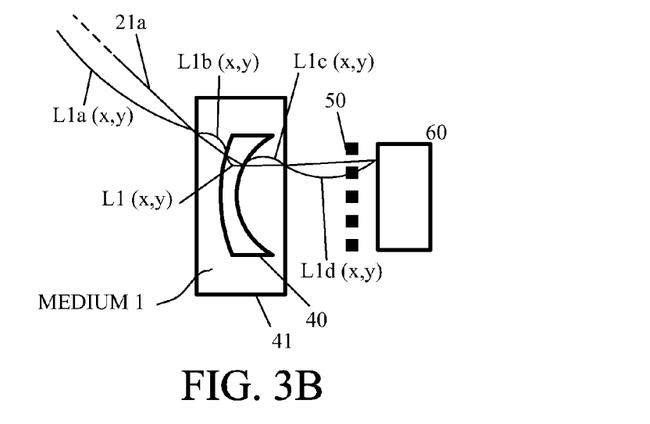

$L_{1a}(x,y)$ to $L_{1d}(x,y)$ represent geometric distances between the above-described constituent elements along a light ray 21a of the reference light shown in FIG. 3B. The light ray 21a passes a certain point (x,y) in the object 40 shown in FIG. 3A. The distance $L_1(x,y)$ is a geometric length (distance) of an optical path of the light ray 21a in the object 40, that is, a geometric thickness of the object 40 along the light ray 21a.

The distance $L_1(x,y)$ can be calculated by means of ray tracing using the reference object. When calculating the simulation wavefront $W_{sim}$, the calculation processing also calculates the distance $L_1(x,y)$ of an arbitrary point. $N_1$ represents a refractive index of the air, and N(0,0) represents a refractive index of the reference object. The refractive index N(0,0) corresponds to an averaged refractive index of a center coordinate (0,0) of the object 40 when the averaging thereof is performed in the optical axis direction. It is necessary to examine the refractive index N(0,0) by another measuring method.

Next, the calculation processing measures the transmitted wavefront in the state where the object 40 is soaked in the air (first medium) in the measuring apparatus shown in FIG. 1A (step S32). This step S32 includes image capturing processing for capturing an image of interference fringes by the CCD 60 and image retrieval processing for retrieving the transmitted wavefront by a processing circuit (not shown). The image retrieval processing of the transmitted wavefront (hereinafter referred to as the "wavefront retrieval") is executed by an FFT (fast Fourier transformation) method.

The wavefront retrieval by the FFT method utilizes a property of aberration that disturbs a carrier fringe of the interference fringes to separate the carrier fringe from the aberration. Specifically, the wavefront retrieval performs a two-dimensional FFT on the interference fringes to convert it into a frequency map. Next, the wavefront retrieval extracts part in the vicinity of the career frequency from the frequency map to perform coordinate transformation thereof such that the career frequency becomes a coordinate origin, and then performs iFFT (inverse fast Fourier transformation). This processing enables calculation of a phase term of a complex amplitude map, and a phase map thus obtained shows the transmitted wavefront.

$W_m$ is expressed by using $L_{1a}(x,y)$ to $L_{1d}(x,y)$ shown in FIG. 3B as the following expression (4):

$$W_m = \{L_{1a}(x,y) + N_1 L_{1b}(x,y) + N(x,y)[L_1(x,y) + dL(x,y)] + N_1[L_{1c}(x,y) - dL(x,y)] + L_{1d}(x,y)\} - \{L_{1a}(0,0) + N_1 L_{1b}(0,0) + N(0,0)[L_1(0,0) + dL(0,0)] + N_1[L_{1c}(0,0) + dL(0,0)] + L_{1d}(0,0)\} \quad (4)$$

In the expression (4), N(x,y) represents a refractive index averaged in a proceeding direction of the light ray 21a at a certain point whose coordinate is (x,y) on the object 40. dL(x,y) represents a thickness error component (shape error component) of the object 40 in the proceeding direction of the light ray 21a. Values of $L_{1a}(x,y)$ to $L_{1d}(x,y)$ and $L_1(x,y)$ in the expressions (3) and (4) are equal to each other because an optical path difference between in a case where a refractive index distribution exists and in a case where it does not exist is negligible small.

The calculation processing calculates at the end of step A a wavefront corresponding to a difference between the simulation wavefront $W_{sim}$ obtained at step S31 and the transmitted wavefront $W_m$ obtained at step S32. That wavefront is expressed by the following expression (5):

$$W_m - W_{sim} = (N(x,y) - N(0,0))L_1(x,y) + (N(x,y) - N_1) dL(x,y) - (N(0,0) - N_1)dL(0,0) \quad (5)$$

Then, the calculation processing performs approximation shown by the following expression (6) to calculate the first transmitted wavefront $W_1$ (step S33). The following expression (7) shows a relationship between the internal refractive index distribution GI and the first transmitted wavefront $W_1$.

$$(N(x,y) - N(0,0))dL(x,y) \approx 0 \quad (6)$$

$$W_1 = GI \cdot L_1(x,y) + (N(0,0) - N_1)dL(x,y) - (N(0,0) - N_1)dL(0,0)$$

$$GI = N(x,y) - N(0,0) \quad (7)$$

The above-described first measuring step (first measurement) in the refractive index distribution measuring method of this embodiment provides the first transmitted wavefront $W_1$ as its measurement result.

Next, as shown in FIG. 1B, the procedure fills the inside of the object case 41 with the water, and places the object 40 therein (step S40). The water is shown as "MEDIUM 2" in FIG. 2. Then, the procedure changes, as at step S20, the NA of the reference light such that the reference light (transmitted light) after being transmitted through the object 40 is brought closer to collimated light than the reference light before entering the object 40 (step S50). The refractive index of the water is larger than that of the air, and therefore the distance between the second collimator lens 31 and the object 40 in the optical axis direction is shorter in the case where the object 40 is soaked in the water than that in the case where the object 40 is soaked in the air.

Next, the calculation processing calculates the simulation wavefront $W_{sim}$ when the object 40 soaked in the water is assumed to have the ideal internal refractive index distribution (step S31). Then, the calculation processing measures the transmitted wavefront $W_m$ in the state where the object 40 is soaked in the water (step S32), and calculates a second transmitted wavefront (second wavefront aberration) $W_2$ corresponding to a difference between the simulation wavefront $W_{sim}$ and the transmitted wavefront $W_m$ (step S33). The second transmitted wavefront $W_2$ is expressed by the following expression (8):

$$W_2 = GI \cdot L_2(x,y) + (N(0,0) - N_2)dL(x,y) - (N(0,0) - N_2)dL(0,0) \quad (8)$$

In the expression (8), $N_2$ represents a refractive index of the water, and $L_2(x,y)$ presents a geometric length (distance) of an optical path of the light ray 21a in the object 40, in other words, a geometric thickness of the object 40 along the light ray 21a. $L_2(x,y)$ can be also calculated by means of the ray tracing when calculating the simulation wavefront $W_{sim}$. The above-described second measuring step (second measurement) in the refractive index distribution measuring method of this embodiment provides the second transmitted wavefront $W_2$ as its measurement result.

As described above, in the first and second measuring steps, the procedure sets (changes) the NA of the reference light such that the transmitted light from the object 40 is brought close to collimated light. Thus, when the coordinate of the certain point (same point) in a peripheral portion in the object 40 away from a central portion thereof on the optical axis is defined as (x,y), the values of $L_1(x,y)$ and $L_2(x,y)$ are inevitably different from each other. In other words, when the light ray 21a passing the first medium and the point (x,y) is defined as a first light ray and the light ray 21a passing the second medium and the point (x,y) is defined as a second light ray, proceeding directions (that is, inclinations with respect to the optical axis) of these first and second light rays are different from each other. In further other words, optical paths of the first and second light rays intersect with each other at the point (x,y) in the object 40.

Thus, this embodiment changes the NA of the reference light to cause the first and second light rays to proceed in the directions different from each other in the first and second measuring steps, which brings the reference light (transmitted light) after being transmitted through the object 40 closer to collimated light as compared with the reference light before entering the object 40 in each measuring step.

The wording "bring the transmitted light close to collimated light" described in this embodiment means that it is desirable that the transmitted light be brought to collimated light but it may be brought to non-collimated light. That is, the transmitted light may be brought to slightly divergent light or slightly convergent light. In this case, it is desirable that, of the transmitted light, a light component (partial light) within an optical axis side 50 percent of an effective light flux diameter (effective diameter) in the transmitted wavefront measurement be brought to collimated light. The optical axis side 50 percent can be also called the "center side 50 percent".

Next, the calculation processing removes by the following expression (9) the shape error component $dL(x,y)$ of the object 40 from the first transmitted wavefront $W_1$ obtained by the expression (7) and the second transmitted wavefront $W_2$ obtained by the expression (8). This enables extraction of the internal refractive index distribution GI of the object 40.

$$GI = \frac{(N(0,0) - N_1)W_2 - (N(0,0) - N_2)W_1}{(N(0,0) - N_1) - (N(0,0) - N_2)} \cdot \frac{1}{L_{eff}(x,y)} \quad (9)$$

$$L_{eff}(x,y) = \frac{(N(0,0) - N_1)L_2(x,y) - (N(0,0) - N_2)L_1(x,y)}{(N(0,0) - N_1) - (N(0,0) - N_2)}$$

In the expression (9), $L_{eff}(x,y)$ represents an effective thickness of the object 40 obtained from $L_1(x,y)$ and $L_2(x,y)$ which are the geometric thicknesses of the object 40 along the first and second light rays. When $L_1(x,y)$ is equal to $L_2(x,y)$, that is, when the proceeding directions (inclinations) of the first and second light rays are identical to each other, $L_{eff}(x,y)$ is equal to each of $L_1(x,y)$ and $L_2(x,y)$.

Thus, the effective thickness $L_{eff}(x,y)$ of the object 40 can be calculated by using $L_1(x,y)$ and $L_2(x,y)$ obtained by the ray tracing.

Finally, the calculation processing calculates the internal refractive index distribution GI of the object 40 by using the first and second transmitted wavefronts $W_1$ and $W_2$ respectively obtained at step S30 and step S60 and $L_{eff}(x,y)$ (step S70).

Step S20 and step S50 executed to bring the transmitted light from the object 40 close to collimated light provide an effect of lowering a measurement error of the refractive index distribution of the object 40 caused due to various geometric errors in the measuring apparatus. For example, an influence of the alignment error of the CCD 60 on the refractive index distribution measurement will be described below.

Figures 4A, 4B:
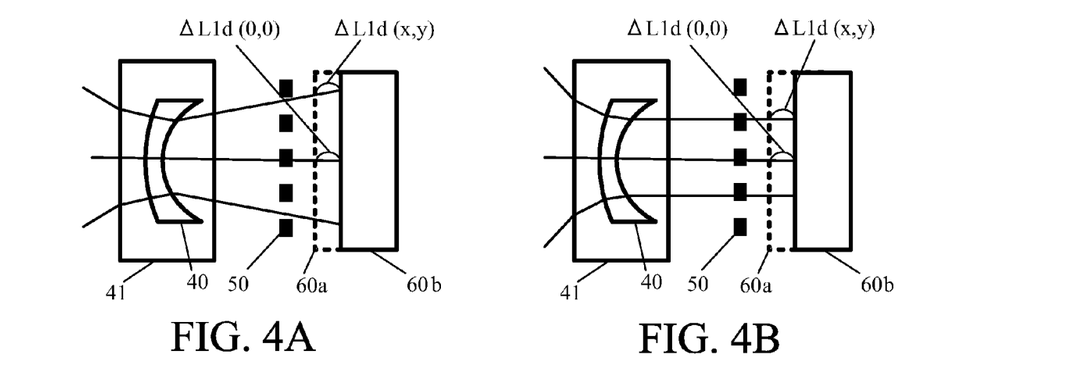
FIGS. 4A and 4B show a change of an optical path length in a case where a CCD position includes an error.

FIGS. 4A and 4B show changes in optical path length when an alignment position of the CCD 60 shifts from a position 60a to a position 60b. FIG. 4A shows a case where the NA of the transmitted light is large, and FIG. 4B shows a case where the NA thereof is small. In these figures, $\Delta L_{1d}(x,y)$ represents a change amount of the optical path length of the light ray 21a caused due to the alignment error of the CCD 60. A difference between $\Delta L_{1d}(x,y)$ and $\Delta L_{1d}(0,0)$ is added to the refractive index distribution as the measurement error. The measurement error of the refractive index distribution increases as the NA of the transmitted light increases (that is, the measurement error decreases as the NA decreases), and it becomes 0 when the transmitted light is completely collimated light.

Such a relationship between the measurement error of the refractive index distribution and the NA of the transmitted light applies to not only the alignment error of the CCD 60, but also to an error of the distance between the second collimator lens 31 and the object 40, an error of the thickness of the object 40, an error of the thickness of the wall of the object case 41 and an error of a distance between the wall of the object case 41 and the object 40. Moreover, the relationship also applies to an error of a distance between the object 40 and the diffraction grating 50, an error of the Talbot distance and an error of a grating period of the diffraction grating 50.

Figure 5:
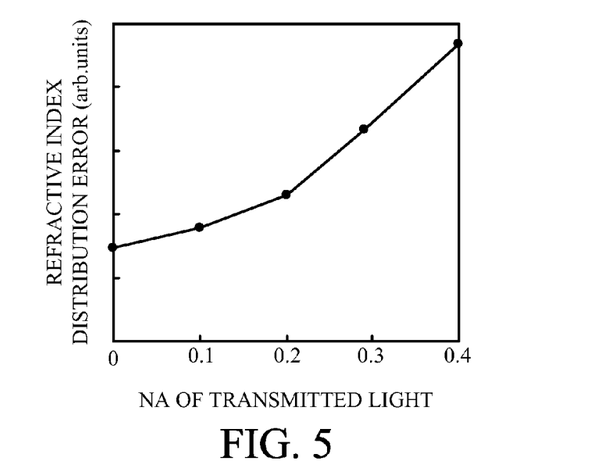
FIG. 5 shows a relationship between an NA of light transmitted through the object and an error of the refractive index distribution.

FIG. 5 shows the relationship between the measurement error of the refractive index distribution and the NA of the transmitted light resulted from the following simulation method.

First, consideration will be made of an object having a certain refractive index distribution (for example, a refractive index distribution that changes in a quadratic function manner from a central portion of the object on the optical axis toward a peripheral portion thereof). The simulation method places each optical element as shown in FIGS. 1A and 1B, and adjusts the distance between the second collimator lens 31 and the object 40 to set the NA of the transmitted light from the object 40 to a certain value (for example, NA=0).

Next, the simulation method provides alignment errors to the optical elements independently, and calculates the refractive index distributions of the respective optical elements. Each of these refractive index distributions includes an error. The simulation method separately calculates refractive index distributions of the respective optical elements in a case where the optical elements are ideally arranged without the alignment errors, and then calculates for each of the optical elements a difference between the refractive index distribution in the case where the alignment error is provided and the refractive index distribution in the case where the alignment error is not provided.

This simulation method enables calculation of the measurement error of the refractive index distribution as an amount corresponding to, for example, the difference between the above-mentioned $\Delta L_{1d}(x,y)$ and $\Delta L_{1d}(0,0)$ in the case where the alignment error is provided to the CCD 60. In addition, this simulation method enables, by calculating a root sum square of the differences calculated for the respective optical elements between the refractive index distribution in the case where the alignment error is provided and the refractive index distribution in the case where the alignment error is not provided, calculation of the measurement error of the refractive index distribution caused in the measuring apparatus.

The simulation method performs similar calculations for other NAs, and plots the calculated measurement errors of the refractive index distribution (refractive index distribution errors) caused in the measuring apparatus in a graph where its horizontal axis represents the NA and its vertical axis represents the refractive index distribution error as shown in FIG. 5.

FIG. 5 shows that the measurement errors of the refractive index distribution decreases as the NA of the transmitted light from the object 40 decreases. FIG. 5 also shows that a gradient of the measurement error of the refractive index distribution with respect to the NA decreases when the NA is 0.2 or less, and the measurement error becomes a minimum value when the NA is 0 (that is, the transmitted light is collimated light). Therefore, bringing the transmitted light from the object 40 as close as possible to collimated light makes it possible to perform highly accurate refractive index distribution measurement.

Figure 6A:
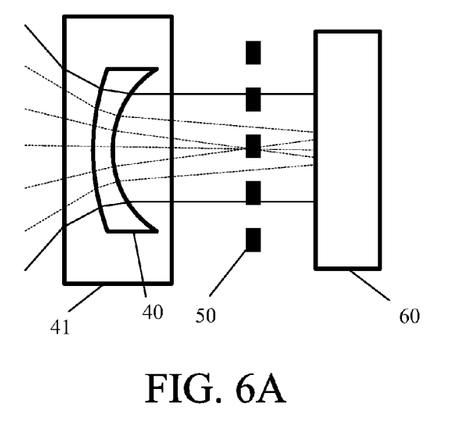
FIGS. 6A and 6B show states of light transmitted through the object in a case where spherical aberration of the object is large.

FIGS. 6A and 6B show the transmitted light from an object having a large spherical aberration. When the spherical aberration is large, setting the NA to 0 may cause light rays transmitted through the vicinity of a central portion of the object 40 to intersect with each other as shown in FIG. 6A. In this case, discrimination of where light rays reaching the CCD 60 have passed in the object 40 cannot be made.

Figure 6B:
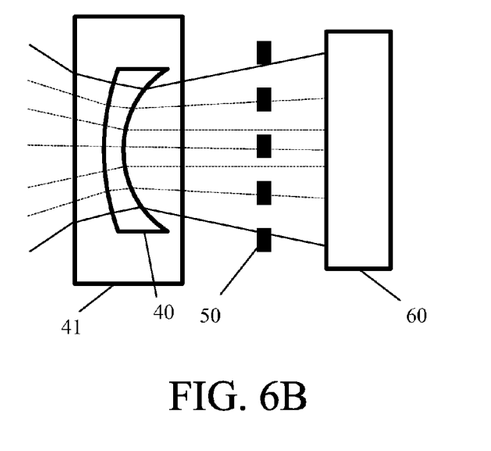

Therefore, when the spherical aberration of the object 40 is large, it is desirable to adjust the arrangement of the illumination optical system such that the transmitted light transmitted through the vicinity of the central portion of the object 40 be brought close to collimated light as shown in FIG. 6B. For example, as described above, it is desirable to adjust the arrangement of the illumination optical system such that the light component within the optical axis side (center side) 50 percent of the effective diameter of the transmitted light be brought to collimated light.

However, it is more desirable to set the NA to 0.2 or less such that at least the gradient of the refractive index distribution error with respect to the NA becomes smaller than that shown in FIG. 5 so as to enable highly accurate refractive index distribution measurement.

Description will hereinafter be made of advantages of bringing the transmitted light from the object 40 close to collimated light on measurement accuracy.

Bringing the transmitted light from the object 40 close to collimated light in the first and second measurement steps causes the first and second light rays to proceed on optical paths different from each other in the object 40. Therefore, the values of N(x, y) on the optical paths of the first and second light rays in the object 40 are also mutually different. When a refractive index in the proceeding direction of the first light ray is defined as N(x,y), and a refractive index in the proceeding direction of the second light ray is defined as N(x,y)+$\Delta$N (x,y), a measurement error $\Delta$GI of the internal refractive index distribution GI caused due to $\Delta$N(x,y) is expressed by the following expression (10):

$$\Delta GI = \frac{(N(0,0)-N_1)L_2(x,y)}{(N(0,0)-N_1)L_2(x,y)-(N(0,0)-N_2)L_1(x,y)}\Delta N(x,y) \quad (10)$$

To decrease the measurement error $\Delta$GI expressed by the expression (10), it is necessary to reduce $\Delta$N(x,y). $\Delta$N(x,y) increases as the optical path of the first light ray and the optical path of the second light ray are further away from each other. For example, when a coordinate (x,y) of a same point where the optical paths of the first and second light rays pass is located on a front surface or a back surface of the object 40, the optical paths of the first and second light rays are furthest away from each other, so that $\Delta$N(x,y) becomes maximum. On the other hand, when the coordinate (x,y) is located near an intermediate point between the front surface and the back surface of the object 40, the optical paths of the first and second light rays are closest to each other, so that $\Delta$N(x,y) becomes small.

Thus, it is desirable to adjust the effective diameter of the reference light 21 such that, in the peripheral portion of the object 40 where spread between the optical paths is particularly large, the optical paths are brought as close as possible to each other. An optimum effective diameter of the reference light 21 can be determined from coordinates where the optical paths pass in the object 40, the coordinates being obtained by performing ray tracing of marginal light rays in each medium. To apply the effective diameter to the measurement, it is desirable to adjust a light flux diameter of the reference light 21 by placing a diaphragm between the pinhole 20 and the object 40. Moreover, instead of such adjustment of the effective diameter of the reference light 21, an analysis area of the effective diameter of the reference light 21, that is, of the transmitted wavefront $W_m$ may be adjusted.

Conforming the optical paths (proceeding directions) of the first and second light rays in the object 40 to each other makes the measurement error $\Delta GI$ expressed by the expression (10) zero. However, conforming the optical paths of the first and second light rays in the object 40 brings the transmitted light from the object 40 away from collimated light, which is the opposite to bringing the transmitted light from the object 40 close to collimated light. Further, the error caused due to the NA of the transmitted light (that is, due to bringing the transmitted light away from the collimated light) is larger than the error shown by the expression (10). Thus, bringing the transmitted light from the object 40 close to collimated light provides a greater effect on improvement of the measurement accuracy as compared with the case of conforming the optical paths of the first and second light rays to each other in the object 40.

[Embodiment 2]

Embodiment 1 described the refractive index distribution measuring method that adjusts the position of the optical element closest to the object 40 in the illumination optical system illuminating the object 40 (that is, the distance between that optical element and the object 40) to change the NA of the reference light. In contrast thereto, a refractive index distribution measuring method that is a second embodiment (Embodiment 2) of the present invention interchanges the optical element closest to the object 40 in the illumination optical system to change the NA of the reference light.

Figure 7A:
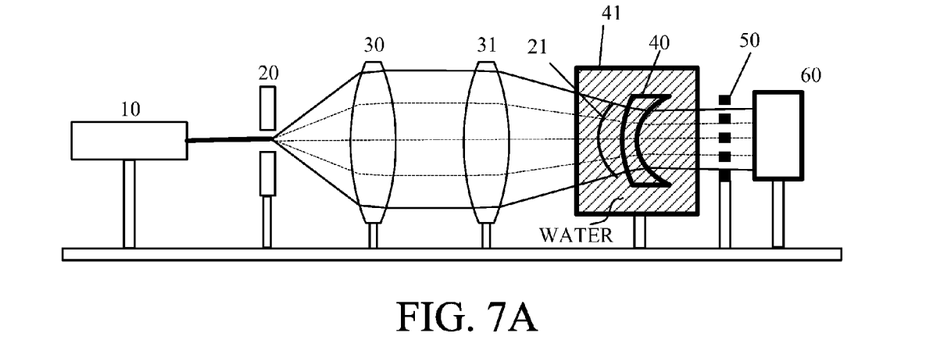
FIGS. 7A and 7B show a configuration of a refractive index distribution measuring apparatus practicing a refractive index distribution measuring method that is Embodiment 2 of the present invention.
Figure 7B:
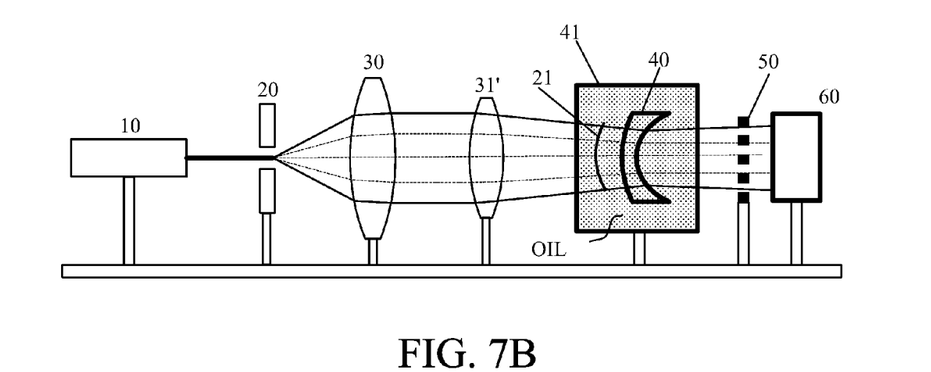

FIGS. 7A and 7B show a configuration of the refractive index distribution measuring apparatus in which the refractive index distribution measuring method of Embodiment 2 is practiced. An object 40 is an optical element such as a lens having a negative optical power. Two media filling an object case 41 in this embodiment are water (first medium) and oil (second medium).

Laser light emitted from a laser light source passes through a pinhole 20 to be brought to an ideal spherical wave. The laser light is transmitted through a first collimator lens 30 and a second collimator lens 31(31') to be converted into convergent light. The second collimator lenses 31(31') is an optical element closest to the object 40 in the illumination optical system that illuminates the object also in this embodiment, and further it can be interchanged. The convergent light is transmitted through the object 40 placed in the object case 41. The light transmitted through the object 40 (hereinafter referred to as the "transmitted light") is brought to approximately collimated light as in Embodiment 1. Then, a transmitted wavefront of the transmitted light is measured by a Talbot interferometer (specifically, by a diffraction grating 50 and a CCD 60) as a wavefront measuring sensor.

Description will hereinafter be made of a procedure of the refractive index distribution measuring method of this embodiment. First, as shown in FIG. 7A, the procedure places (soaks) the object 40 in the water filling the object case 41 (step S10 in FIG. 2). Next, the procedure sets the second collimator lens 31 having an appropriate F-number and an appropriate aperture diameter such that the transmitted light from the object 40 is brought close to collimated light (step S20). For example, when the transmitted light from the object 40 is divergent light, it is desirable to interchange the second collimator lens 31 with another second collimator lens having a small F-number and a large aperture diameter. The second collimator lens 31 may be selected through observation of a light intensity distribution of the transmitted light in the measuring apparatus. In stead of the observation of the light intensity distribution, arrangement design of optical elements in the illumination optical system may be made in advance such that the transmitted light is brought close to collimated light, and then the second collimator lens 31 may be selected on the basis of the designed arrangement.

Next, the procedure (calculation processing) calculates a first transmitted wavefront (first wavefront aberration) $W_1$ when the medium in the object case 41 is the water, with same processes as those in step A described in Embodiment 1 (step S30).

Next, as shown in FIG. 7B, the procedure places (soaks) the object 40 in the oil filling the object case 41 (step S40). A refractive index of the oil is different from that of the water. Then, the procedure interchanges the second collimator lens 31 with a second collimator lens 31' having an appropriate F-number and an appropriate aperture diameter such that the transmitted light from the object 40 is brought close to collimated light (step S50). For example, when the refractive index of the oil is higher than that of the water, it is desirable to interchange the second collimator lens 31 with the second collimator lens 31' having a larger F-number and a smaller aperture diameter than those of the second collimator lens 31.

Next, the procedure (calculation processing) calculates a second transmitted wavefront (second wavefront aberration) $W_2$ when the medium in the object case 41 is the oil (step S60) according to step A.

Finally, the calculation processing calculates an effective thickness of the object 40 by using the expression (9), and further calculates an internal refractive index distribution GI of the object (step S70).

[Embodiment 3]

Embodiments 1 and 2 described the refractive index distribution measuring method adjusting the position of the optical element closest to the object 40 in the illumination optical system illuminating the object 40 or interchanging the optical element, to change the NA of the reference light. In contrast thereto, a refractive index distribution measuring method that is a third embodiment (Embodiment 3) of the present invention adjusts a refractive index of a medium filling an object case 41 to change the NA of the reference light.

Figure 8A:
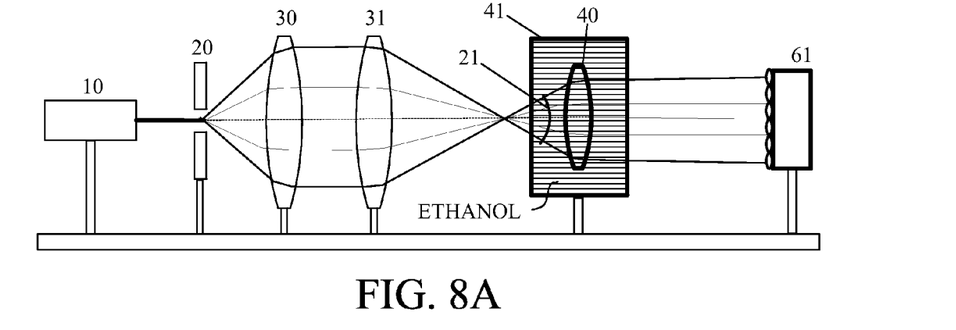
FIGS. 8A and 8B show a configuration of a refractive index distribution measuring apparatus practicing a refractive index distribution measuring method that is Embodiment 3 of the present invention.
Figure 8B:
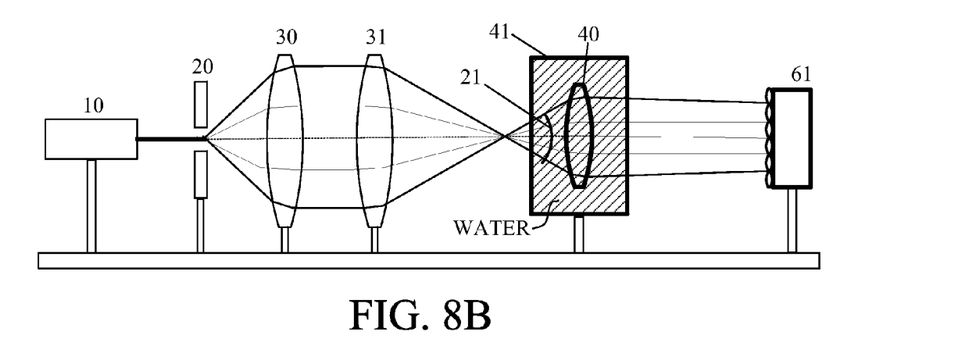

FIGS. 8A and 8B show a configuration of the refractive index distribution measuring apparatus in which the refractive index distribution measuring method of Embodiment 3 is practiced. An object 40 is an optical element such as a lens having a positive optical power.

Laser light emitted from a laser light source passes through a pinhole 20 to be brought to an ideal spherical wave. The laser light is transmitted through a first collimator lens 30 and a second collimator lens 31 to be converted into convergent light. The convergent light converges once and then diverges.

The divergent light is transmitted through the object 40 placed in the object case 41. The light transmitted through the object 40 (hereinafter referred to as the "transmitted light") is brought to approximately collimated light. Then, a transmitted wavefront of the transmitted light is measured by a Shack- Hartmann Sensor 61 as a wavefront measuring sensor. In a case where the object 40 is an optical element having a positive power, the divergent light from the pinhole 20 may directly enter the object 40 without passing through the first and second collimator lenses 30 and 31.

Description will hereinafter be made of a procedure of the refractive index distribution measuring method of this embodiment. First, the procedure places the object 40 in the object case 41 and fills the object case 41 with the first medium having an appropriate refractive index such that the transmitted light from the object 40 is brought close to collimated light (steps S10 and S20 in FIG. 2). For example, when the transmitted light from the object 40 is divergent light in the state where the object case 41 is filled with the first medium, it is desirable to interchange the first medium with another first medium having a higher refractive index. On the other hand, when the transmitted light from the object 40 is convergent light in the state where the object case 41 is filled with the first medium, it is desirable to interchange the first medium with another first medium having a lower refractive index. The first medium may be selected through observation of a light intensity distribution of the transmitted light in the measuring apparatus. In stead of the observation of the light intensity distribution, arrangement design of optical elements in the illumination optical system may be made in advance such that the transmitted light is brought close to collimated light, and then the first medium may be selected on the basis of the designed arrangement.

FIG. 8A shows a case where the first medium selected such that the transmitted light is brought close to collimated light is ethanol. The procedure (calculation processing) calculates a first transmitted wavefront (first wavefront aberration) $W_1$ when the medium in the object case 41 is ethanol, with same processes as those in step A described in Embodiment 1 (step S30).

Next, the procedure places the object 40 in the object case 41 and fills the object case 41 with the second medium having an appropriate refractive index such that the transmitted light from the object 40 is brought close to collimated light (steps S40 and S50). The refractive index of the second medium is different from that of the first medium. However, in a case where a distance between the second collimator lens 31 and the object 40 in an optical axis direction is not changed, the refractive index of the second medium inevitably becomes close to that of the first medium. It is possible to use as the first and second media a same material whose refractive index is changed by adjusting its temperature.

FIG. 8B shows a case where the second medium is water. The procedure (calculation processing) calculates a second transmitted wavefront (second wavefront aberration) $W_2$ when the medium in the object case 41 is the water (step S60) according to step A.

Finally, the procedure calculates an effective thickness of the object 40 by using the expression (9), and further calculates an internal refractive index distribution GI of the object 40 (step S70).

[Embodiment 4]

Figure 9:
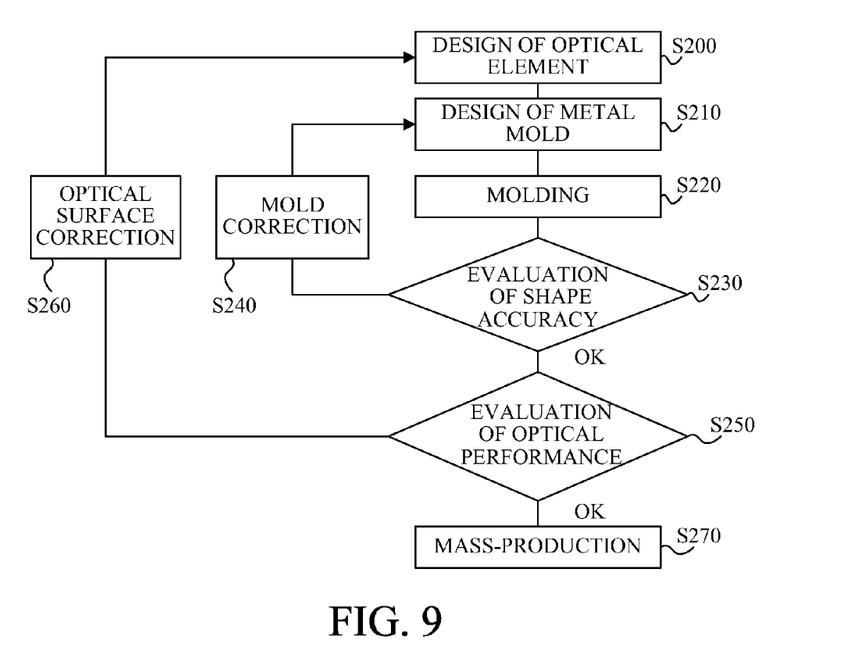
FIG. 9 shows a manufacturing method of an optical element using any one of the refractive index distribution measuring methods of Embodiments 1 to 3.

It is possible to feed back the measurement result obtained by the refractive index distribution measuring apparatus (or the refractive index distribution measuring method) described in any one of Embodiments 1 to 3 to a manufacturing method of an optical element such as a lens. FIG. 9 shows an example of the manufacturing method of the optical element using molding.

In FIG. 9, Step S200 is a step of designing the optical element where a designer designs the optical element by using optical design software.

Step S210 is a step of designing and processing a metal mold for molding the optical element on the basis of the optical element design made at step S200.

Step S220 is a step of molding the optical element by using the metal mold processed at step S210.

Step S230 is a step of measuring a shape of the optical element molded at step S220 and evaluating accuracy thereof. If the shape evaluated at step S230 does not satisfy required accuracy, the manufacturing method calculates at step S240 a correction amount of the metal mold, and then reprocesses at step S210 the metal mold by using the correction amount.

Step S250 is a step of evaluating optical performance of the optical element satisfying the required accuracy in shape at step S230. The manufacturing method executes at step S250 the refractive index distribution calculation processing described in FIG. 2, and evaluates the optical performance of the optical element by using the calculation result. If the optical performance evaluated at step S250 does not satisfy required specifications, the manufacturing method calculates at step S260 correction amounts of optical surfaces of the optical element, and redesigns at step S200 the optical element by using the correction amounts.

Step S270 is a step of mass-producing the optical element under optical element manufacturing conditions that can achieve the required optical performance at step S250.

The optical element manufacturing method of this embodiment enables accurate measurement of the internal refractive index distribution of the optical element, which makes it possible to mass-produce the optical elements accurately by molding even when the optical element is formed of a high refractive index glass material.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-262468, filed Nov. 18, 2009 which is hereby incorporated by reference herein in its entirety.

What is claimed is:

1. A refractive index distribution measuring method comprising:

a first measuring step of placing an object in a first medium whose refractive index is lower than a refractive index of the object, and of causing reference light to enter the object to measure a first transmitted wavefront of the object;

a second measuring step of placing the object in a second medium whose refractive index is lower than the refractive index of the object and different from the refractive index of the first medium, and of causing the reference light to enter the object to measure a second transmitted wavefront of the object; and a calculating step of calculating an internal refractive index distribution of the object by a computing unit, wherein, when, of the reference light entering the object in the first measuring step, a light ray entering a peripheral portion of the object which is away from a central portion thereof which is located on an optical axis and passing through a certain point of the object is defined as a first light ray, and of the reference light entering the object in the second measuring step, a light ray entering the peripheral portion and passing through the certain point is defined as a second light ray, in the first and second measuring steps, the method causes the first and second light rays to proceed in directions different from each other to change a numerical aperture of the reference light such that the reference light after being transmitted through the object is brought closer to collimated light than the reference light before entering the object, and wherein, in the calculating step, the method calculates an effective thickness of the object by using geometric thicknesses of the object along the respective first and second light rays, and calculates the internal refractive index distribution of the object by using the first and second transmitted wavefronts measured in the first and second measuring steps and the calculated effective thickness.

2. A refractive index distribution measuring method according to claim 1, wherein, in the first and second measuring steps, the method changes the numerical aperture such that partial light of the reference light after being transmitted through the object is brought closer to collimated light, the partial light corresponding to a light component within an optical axis side 50 percent of an effective diameter of the reference light.

3. A manufacturing method of an optical element, the method comprising:

a forming step of molding the optical element; and an evaluating step of evaluating the optical element, wherein, in the evaluating step, the method measures the internal refractive index distribution of the optical element by using a refractive index distribution measuring method according to claim 1.

4. A refractive index distribution measuring apparatus comprising:

a measuring part configured to perform a first measurement that causes reference light to enter an object placed in a first medium whose refractive index is lower than a refractive index of the object to measure a first transmitted wavefront of the object, and to perform a second measurement that causes the reference light to enter the object placed in a second medium whose refractive index is lower than the refractive index of the object and different from the refractive index of the first medium to measure a second transmitted wavefront of the object; and a calculating part configured to calculate an internal refractive index distribution of the object, wherein, when, of the reference light entering the object in the first measurement, a light ray entering a peripheral portion of the object which is away from a central portion thereof which is located on an optical axis and passing through a certain point of the object is defined as a first light ray, and of the reference light entering the object in the second measurement, a light ray entering the peripheral portion and passing through the certain point is defined as a second light ray, the measuring part is configured to causes the first and second light rays to proceed in directions different from each other to change a numerical aperture of the reference light such that the reference light after being transmitted through the object is brought closer to collimated light than the reference light before entering the object, and wherein the calculating part is configured to calculate an effective thickness of the object by using geometric thicknesses of the object along the respective first and second light rays, and calculates the internal refractive index distribution of the object by using the first and second transmitted wavefronts measured in the first and second measurements and the calculated effective thickness.

\* \* \* \* \*